Figure 1:
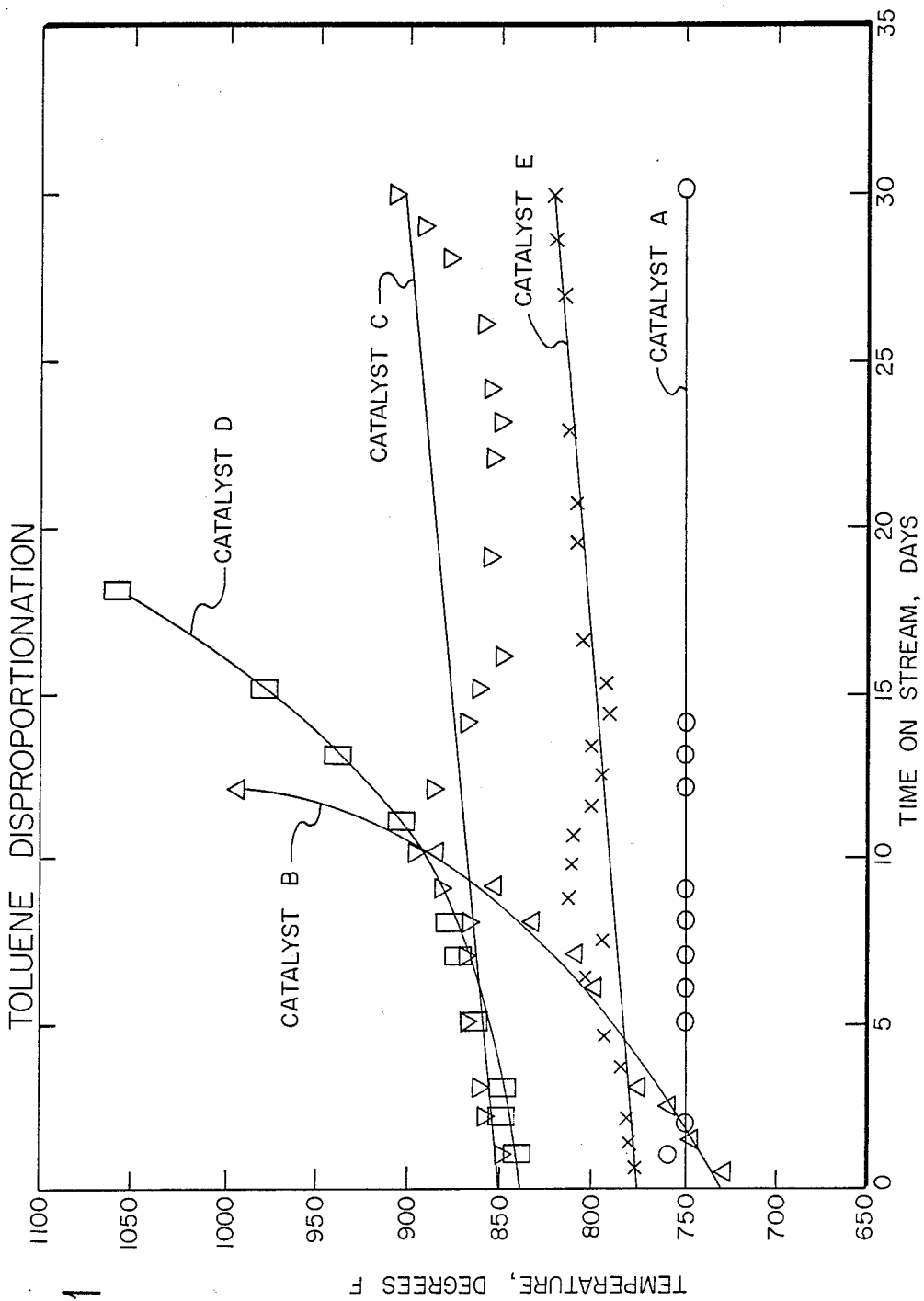

United States Patent [19]

Absil et al.

[11] Patent Number: 4,851,604
[45] Date of Patent: Jul. 25, 1989

[54] TOLUENE DISPROPORTIONATION

[75] Inventors: Robert P. L. Absil, Mantua; Scott Han, Lawrenceville; David O. Marler, Deptford; David S. Shihabi, Pennington, all of N.J.

[73] Assignee: Mobil Oil Corp., New York, N.Y.

[21] Appl. No.: 92,842

[22] Filed: Sep. 2, 1987

[51] Int. Cl.[4] ............................................. C07C 5/22
[52] U.S. Cl. .................................................. 585/475
[58] Field of Search ........................................ 585/475

[56] References Cited

U.S. PATENT DOCUMENTS

| | | | |
|---|---|---|---|
| 3,413,374 | 11/1968 | Sato et al. | 260/672 |
| 3,598,878 | 8/1971 | Kovach et al. | 260/672 |
| 3,598,879 | 8/1971 | Kmecak et al. | 260/672 |
| 3,607,961 | 9/1971 | Kovach et al. | 260/672 R |
| 3,965,207 | 6/1976 | Weinstein | 260/671 M |
| 3,965,208 | 6/1976 | Butter et al. | 260/671 M |
| 3,965,209 | 6/1976 | Butter et al. | 260/671 M |
| 4,001,346 | 1/1977 | Chu | 260/671 M |
| 4,002,698 | 1/1977 | Kaeding | 260/671 M |
| 4,007,231 | 2/1977 | Butter | 260/672 T |
| 4,011,276 | 3/1977 | Chu | 260/672 T |
| 4,016,219 | 4/1977 | Kaeding | 260/672 T |
| 4,029,716 | 6/1977 | Kaeding | 260/672 T |
| 4,052,476 | 10/1977 | Morrison | 260/672 T |
| 4,067,920 | 1/1978 | Kaeding | 260/671 M |
| 4,097,543 | 6/1978 | Haag et al. | 585/475 |
| 4,100,215 | 7/1978 | Chen | 260/671 M |
| 4,117,026 | 9/1978 | Haag et al. | 260/671 R |
| 4,152,364 | 5/1979 | Chu | 585/454 |
| 4,380,685 | 4/1983 | Chu | 585/466 |
| 4,547,605 | 10/1985 | Kresge et al. | 585/467 |
| 4,599,475 | 7/1986 | Kresge et al. | 585/481 |
| 4,677,239 | 6/1987 | Dewing et al. | 585/475 |
| 4,694,114 | 9/1987 | Chu et al. | 585/481 |

OTHER PUBLICATIONS

Otani, Seiya, "Benzene, Xylene Bonanza from Less-Prized Aromatics", Chemical Engineering, Jul. 27, 1970, pp. 118-120.

Grandio, P. and Schneider, F. H., "AP-Catalyst Processes Make Aromatics at Low Temperatures", The Oil and Gas Journal, Nov. 29, 1971, pp. 62-29.

Primary Examiner—Curtis R. Davis
Attorney, Agent, or Firm—Alexander J. McKillop; Charles J. Speciale; Dennis P. Santini

[57] ABSTRACT

An improved process is provided for vapor-phase disproportionation of toluene over catalyst comprising a molecular sieve having a high lattice aluminum content whereby its silica/alumina mole ratio is less than 55 and a diffusion rate constant of less than about 150 sec$^{-1}$.

15 Claims, 1 Drawing Sheet

TOLUENE DISPROPORTIONATION

CROSS-REFERENCE

This application is related by subject matter to the following applications filed on even date herewith:
Ser. No. 092,504
Ser. No. 092,503

BACKGROUND OF THE INVENTION

1. Field of the Invention

This invention is directed to an improved process for vapor-phase disproportionation of toluene in the presence of catalyst comprising a crystalline molecular sieve characterized by a silica/alumina mole ratio of at least about 12 and a Constraint Index of from about 1 to about 12. The improvement comprises use of a molecular sieve catalyst component having a high lattice aluminum content whereby its silica/alumina mole ratio is less than 55 and a diffusion rate constant of less than 150 $\text{sec}^{-1}$.

2. Description of the Prior Art

Zeolitic materials, both natural and synthetic, have been demonstrated in the past to have catalytic properties for various types of hydrocarbon conversions. Certain zeolitic materials are ordered, porous crystalline molecular sieves having a definite crystalline structure within which there are a large number of smaller cavities which may be interconnected by a number of still smaller channels. Since the dimensions of these pores are such as to accept for adsorption molecules of certain dimensions while rejecting those of larger dimensions, these materials have come to be known as "molecular sieves" and are utilized in a variety of ways to take advantage of these properties.

Prior art techniques have resulted in the formation of a great variety of synthetic molecular sieves. These materials have come to be designated by convenient symbols, as illustrated by ZSM-5 (U.S. Pat. No. 3,702,886).

The use of certain molecular sieves as catalyst components is taught in U.S. Pat. No. 4,305,808, for example.

The silica/alumina molar ratio of a given molecular sieve is often variable; for example, zeolite X (U.S. Pat. No. 2,882,244) can be synthesized with a silica/alumina ratio of from 2 to 3; zeolite Y (U.S. Pat. No. 3,130,007) from 3 to about 6. In some molecular sieves, the upper limit of silica/alumina ratio is virtually unbounded. ZSM-5 is one such material wherein the silica/alumina ratio is at least 5. U.S. Pat. No. 3,941,871 (Re. 29,948) discloses a porous crystalline silicate made from a reaction mixture containing no deliberately added alumina and exhibiting an X-ray diffraction pattern characteristic of ZSM-5. U.S. Pats. Nos. 4,061,724; 4,073,865 and 4,104,294 describe crystalline silicates of varying alumina and metal content.

It is known that zeolites are stabilized for various processes by reducing lattice aluminum content. The FCC applications, for example, the catalyst of choice is ultrastable Y which has been dealuminized from its precursor Y form by steaming. Another example of stability enhancement by catalyst dealuminization is in hydrodewaxing. U.S. Pat. No. 4,247,388 teaches the improvement of catalyst aging characteristics in lube dewaxing by steaming ZSM-5 to reduce lattice aluminum content.

U.S. Pat. No. 4,380,685 teaches para-selective alkylation, transalkylation or disproportionation of a substituted aromatic compound to form a dialkylbenzene compound mixture over catalyst comprising zeolite characterized by a Constraint Index of 1 to 12 and a silica/alumina mole ratio of at least 12/1, the catalyst having thereon incorporated various metals and phosphorus. Other patents covering alkylation and transalkylation include U.S. Pats. Nos. 4,127,616; 4,361,713; 4,365,104; 4,367,359; 4,370,508 and 4,384,155. Toluene is converted to para-xylene in U.S. Pats. Nos. 3,965,207; 3,965,208; 3,965,209; 4,001,346; 4,002,698; 4,067,920; 4,100,215 and 4,152,364, to name a few. Alkylation with olefins is taught, for example, in U.S. Pats. Nos. 3,962,364 and 4,106,218 and toluene is disproportionated in, for example, U.S. Pats. Nos. 4,052,476; 4,007,231; 4,011,276; 4,016,219 and 4,029,716. Isomerization of xylenes is taught in, for example, U.S. Pats. Nos. 4,100,214; 4,101,595; 4,158,676; 4,159,282; 4,351,979; 4,101,597; 4,159,283; 4,152,363; 4,163,028; 4,188,282 and 4,224,141.

U.S. Pats. Nos. 3,551,509 and Re. 27,639 disclose transalkylation between trimethylbenzenes and toluene to yield xylenes and benzene in the presence of a crystalline aluminosilicate catalyst having large pore openings of 8 to 15 Angstrom units and, preferably containing Group VIII metals, hydrogen and rare earth cations.

In the area of aromatic disproportionation, Grandio et al teach in the *Oil and Gas Journal,* Vol. 69, Number 48 (1971) a liquid-phase toluene disproportionation process utilizing zeolite catalysts in the absence of hydrogen. They further teach that vapor-phase toluene disproportionation requires hydrogen recycle or else frequent regeneration of catalyst to keep coke levels low on the catalyst and to maintain catalytic activity over any reasonable period of time.

Otani teaches in *Chemical Engineering,* 77 (16), 118 (1970) that vapor-phase catalytic disproportionation of toluene requires hydrogen recycle to keep the zeolite catalyst from excessive coke build-up and, thereby, maintain reasonable catalyst activity.

U.S. Pats. Nos. 3,126,422; 3,413,374; 3,598,878; 3,598,879 and 3,607,961 show vapor-phase disproportionation of toluene over various catalyst. U.S. Pat. No. 4,117,026, incorporated herein in its entirety by reference, teaches disproportionation over catalyst comprising zeolite having a silica/alumina mole ration of at least 12, a Constraint Index of 1 to 12 and a specified sorption capacity for xylenes.

SUMMARY

This invention contemplates an improved process for effecting vapor-phase toluene disproportionation which comprises contacting a toluene charge under conditions effective for accomplishing said vapor-phase disproportionation, including a reactor inlet temperature between about 600° F. and about 1100° F., a pressure between atmospheric and 1000 psig, a total feed weight hourly space velocity (WHSV) between about 0.1 $\text{hr}^{-1}$ and about 30 $\text{hr}^{-1}$ and a low hydrogen to hydrocarbon mole ratio of from 0 to about 10, with a catalyst composition comprising a crystalline molecular sieve having a high lattice aluminum content characterized by a silica/alumina mole ratio of less than 55, preferably from about 20 to about 40, a Constraint Index from about 1 to about 12 and a diffusion rate constant $(D/r^2 \times 10^6)$ of less than about 150 $\text{sec}^{-1}$, preferably less than about 120 sec$^{-1}$. The above WHSV is based upon the weight of catalyst molecular sieve, i.e. total weight of active catalyst component.

EMBODIMENTS

The present invention relates to an improved vapor-phase toluene disproportionation process. U.S. Pat. No. 4,052,476, incorporated herein by reference in its entirety, is illustrative of a prior art vapor-phase process for disproportionation of toluene over a wide range of conditions and with a catalyst composition comprising a crystalline molecular sieve characterized by a silica/alumina mole ratio of at least 12 and a Constraint Index of from 1 to 12, e.g. ZSM-5, ZSM-11, ZSM-12, ZSM-35 and ZSM-38.

For the present improved process, the catalyst will comprise a crystalline molecular sieve material having a structure which will permit a Constraint Index of from about 1 to about 12. The silica/alumina mole ratio of the molecular sieve for use herein, however, will be less than 55, preferably from about 20 to less than 55, e.g. from about 20 to about 40. The molecular sieve will also display a diffusion rate constant $(D/r^2 \times 10^6)$ of less than about 150 sec$^{-1}$, and preferably less than about 120 sec$^{-1}$. If either the silica/alumina ratio of the diffusion rate constant are not as above, the improvement of this invention will not be realized.

The crystalline molecular sieves which can be made to exhibit the above required properties include those having the structure of ZSM-5, ZSM-11, ZSM-5/ZSM-11 intermediate, ZSM-12, ZSM-22, ZSM-23, ZSM-35, ZSM-38, ZSM-48, ZSM-50 and Beta. ZSM-5 is described in U.S. Pat. No. 3,702,886, the contents of which are incorporated herein by reference. ZSM-11 is described in U.S. Pat. No. 3,709,979, the contents of which are incorporated herein by reference. ZSM-5/ZSM-11 intermediate is described in U.S. Pat. No. 4,229,424, the contents of which are incorporated herein by reference. ZSM-12 is described in U.S. Pat. No. 3,832,449, the contents of which are incorporated herein by reference. ZSM-23 is described in U.S. Pat. No. 4,076,842, the contents of which are incorporated herein by reference. ZSM-35 is described in U.S. Pat. No. 4,016,245, the contents of which are incorporated herein by reference. ZSM-38 is described in U.S. Pat. No. 4,076,859, the contents of which are incorporated herein by reference. ZSM-48 is described in U.S. Pat. No. 4,397,827, the contents of which are incorporated herein by reference. ZSM-50 is described in U.S. Pat. No. 4,640,849, the contents of which are incorporated herein by reference. Beta is described in U.S. Pat. No. 3,308,069, the contents of which are incorporated herein by reference.

ZSM-22 is a molecular sieve which can be made to be useful in the present improved process. In general, its as-synthesized composition is as follows:

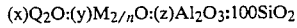

$(x)Q_2O:(y)M_{2/n}O:(z)Al_2O_3:100SiO_2$ wherein $Q_2O$ is the oxide form of an organic compound containing an element of Group VA of the Periodic Table of Elements, e.g. N or P, preferably N, containing at least one alkyl or aryl group having at least 2 carbon atoms, M is an alkali metal or an alkaline earth metal having a valence n, and $x=0.01-2.0$, $y=0-2.0$ and $z=0-5$.

ZSM-22 has a definite X-ray diffraction pattern, set forth below in Table I, which distinguishes it from other crystalline materials.

TABLE I

| Interplanar d-spacings (A) | Relative Intensity (I/Io) |
|---|---|
| 10.9 ± 0.2 | M-VS |
| 8.7 ± 0.16 | W |
| 6.94 ± 0.10 | W-M |
| 5.40 ± 0.08 | W |
| 4.58 ± 0.07 | W |
| 4.36 ± 0.07 | VS |
| 3.68 ± 0.05 | VS |
| 3.62 ± 0.05 | S-VS |
| 3.47 ± 0.04 | M-S |
| 3.30 ± 0.04 | W |
| 2.74 ± 0.02 | W |
| 2.52 ± 0.02 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 $I/I_o$ is the intensity of the strongest line or peak, and d (obs.) the interplanar spacing in Angstroms (A), corresponding to the recorded lines, were determined. In Table I, the relative intensities are given in terms of the symbols VS=very strong, M=medium, W=weak, etc. It should be understood that this X-ray diffraction pattern is characteristic of all the species of ZSM-22. Ion exchange of the alkali metal cations with other ions results in substantially the same X-ray diffraction pattern with some minor shifts in interplanar spacing and variation in relative intensity. Other minor variations can occur, depending on the silica/alumina ratio of the particular sample, as well as its degree of thermal treatment.

ZSM-22 can be suitably prepared from a reaction mixture containing a source of silica, an alkane diamine, an alkali metal oxide or an alkaline earth metal oxide (e.g. sodium, potassium, cesium, calcium or strontium), water, and alumina, and have a composition, in terms of mole ratios of oxides, within the following ratios:

| Reactants | Broad | Preferred |
|---|---|---|
| $SiO_2/Al_2O_3 =$ | 20 or more | 30 to 1000 |
| $H_2O/SiO_2 =$ | 10 to 100 | 20 to 60 |
| $OH^-/SiO_2 =$ | 0 to 0.3 | 0.1 to 0.2 |
| $M^+/SiO_2 =$ | 0 to 2.0 | 0.1 to 1.0 |
| $RN/SiO_2 =$ | 0.01 to 2.0 | 0.05 to 1.0 | wherein RN is a $C_2$–$C_{12}$ alkane diamine of the formula $H_2N$—$(CH_2)_n$—$NH_2$ (abbreviated $C_nDN$), n=2 to 12, and preferably is 5 to 8, and M is an alkali metal or an alkaline earth metal, and maintaining the mixture at crystallization temperature until crystals of ZSM-22 are formed. Thereafter, the crystals are separated from the liquid by an conventional means, washed and recovered.

The original cations of the above molecular sieves are preferably replaced in accordance with techniques well known in the art, at least in part, with hydrogen or hydrogen precursor cations and/or non-noble metal ions of Group VIII of the Periodic Table, e.g. nickel, iron and/or cobalt.

Diffusivities are determined by measuring the time ($t_{0.3}$) it takes to sorb 30% of o-xylene by the rate constant determination test described in U.S. Pat. No. 4,117,026, incorporated herein by reference as to that description. The characteristic diffusion time, $t_{0.3}$, is a direct measure of the critical mass transfer property $r^2/D$.

The members of the class of molecular sieves useful herein have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular molecular sieve solely from theoretical structure considerations.

A convenient measure of the extent to which a crystal provides control to molecules of varying sizes to it internal structure is the Constraint Index of the crystal. Crystalline materials which provide a highly restricted access to and egress from its internal structure have a high value for the Constraint Index, and materials of this kind usually have pores of small size, e.g. less than 5 Angstroms. On the other hand, crystalline materials which provide relatively free access to the internal crystal structure have a low value for the Constraint Index, and usually pores of large size, e.g. greater than 8 Angstroms. The method by which Constraint Index is determined is described fully in U.S. Pat. No. 4,106,218, incorporated by reference for details of the method.

Constraint Index (CI) values for some typical materials are:

|  | CI | (at test temperature) |
| --- | --- | --- |
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |
| ZSM-38 | 2 | (510° C.) |
| ZSM-48 | 3.5 | (538° C.) |
| ZSM-50 | 2.1 | (427° C.) |
| TMA Offretite | 3.7 | (316° C.) |
| TEA Mordenite | 0.4 | (316° C.) |
| Clinoptilolite | 3.4 | (510° C.) |
| Mordenite | 0.5 | (316° C.) |
| REY | 0.4 | (316° C.) |
| Amorphous Silica-alumina | 0.6 | (538° C.) |
| Dealuminized Y | 0.5 | (510° C.) |
| Erionite | 38 | (316° C.) |
| Zeolite Beta | 0.6–2.0 | (316° C.–399° C.) |

The above-described Constraint Index is an important and even critical definition of those molecular sieves which are useful in the instant invention. The very nature of this parameter and the recited technique by which it is determined, however, admit of the possibility that a given material can be tested under somewhat different conditions and thereby exhibit different Constraint Indices. Constraint Index seems to vary somewhat with severity of operations (conversion) and the presence or absence of binders. Likewise, other variables, such as crystal size, the presence of occluded contaminants, etc., may affect the Constraint Index. Therefore, it will be appreciated that it may be possible to so select test conditions, e.g. temperature, as to establish more than one value for the Constraint Index of a particular crystalline material. This explains the range of Constraint Indices for some molecular sieves, such as ZSM-5, ZSM-11 and Beta.

It is to be realized that the above CI values typically characterize the specified crystalline materials, but that such are the cumulative result of several variables useful in the determination and calculation thereof. Thus, for a given crystal exhibiting a CI value within the range of 1 to 12, depending on the temperature employed during the the test method within the range of 290° C. to about 538° C., with accompanying conversion between 10% and 60%, the Ci may vary within the indicated range of 1 to 12. Likewise, other variables such as the crystal size of the material, the presence of possibly occluded contaminants and binders intimately combined with the crystal may affect the CI. It will accordingly be understood to those skilled in the art that the CI, as utilized herein, while affording a highly useful means for characterizing the molecular sieves of interest is approximate, taking into consideration the manner of its determination, with the possibility, in some instances, of compounding variable extremes. However, in all instances, at a temperature within the above-specified range of 290° C. to about 538° C., the CI will have a value for any given molecular sieve of interest herein within the approximate range of 1 to 12.

The molecular sieve for use herein or the catalyst comprising same can be thermally treated at high temperatures. This thermal treatment is generally performed by heating at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product is particularly useful in the present process.

For the improved disproportionation process of this invention the suitable molecular sieve may be employed in combination with a support or binder material such as, for example, a porous inorganic oxide support or a clay binder. Non-limiting examples of such binder materials include alumina, zirconia, silica, magnesia, thoria, titania, boria and combinations thereof, generally in the form of dried inorganic oxide gels and gelatinous precipitates. Suitable clay materials include, by way of example, bentonite and kieselguhr. The relative proportion of suitable crystalline molecular sieve of the total composition of catalyst and binder or support may vary widely with the zeolite content ranging from between about 30 to about 90 percent by weight and more usually in the range of about 50 to about 80 percent by weight of the composition. The composition may be in the form of an extrudate, beads or fluidizable microspheres.

Operating conditions employed in the improved process of the present invention are critical. Such conditions as temperature, pressure, space velocity, molar ratio of the reactants and hydrogen to hydrocarbon mole ratio will have important effects on the process.

The improved process of this invention is conducted such that disproportionation of toluene is carried out in the vapor-phase by contact in a reaction zone, such as, for example a fixed bed of catalyst composition, under disproportionation effective conditions, said catalyst composition being characterized as comprising the above-defined molecular sieve, preferably which has been hydrogen, hydrogen precursor and/or non-noble Group VIII metal exchanged and/or thermally treated. The effluent is separated and distilled to remove desired product, such as benzene and xylene, and unreacted reactant, i.e toluene, is recycled for further reaction.

By the present improved process toluene is converted to aromatic concentrates of high value, e.g. xylene and benzene. This process may be conducted in either batch or fluid bed operation with attendant benefits of either operation readily obtainable.

In the process of this invention, the toluene charge is preferably dried in a manner which will minimize the water entering the reaction employed. Means known in the art suitable for drying the toluene charge to the present process are numerous, including percolation through silica gel, activated alumina, molecular sieves or other suitable substance or use of liquid charge dryers.

In a typical embodiment of the present process, optimum toluene conversion is found to be from about 40 weight percent to about 50 weight percent. Yield of $C_5^-$ products and ring losses in such an embodiment appear to increase at conversion above about 40 percent and xylene yields begin to decrease when toluene conversion exceeds about 50 weight percent.

Considering this vapor-phase disproportionation of toluene, the first stage feed is heated to a temperature within the range of about 600° F. to about 1100° F. at a pressure within the range of about atmospheric to about 1000 psig. Preferred inlet temperatures for the process of the present invention fall within the range of about 650° F. to about 1000° F. and preferred pressures fall within the range of about 50 psig to about 1000 psig. The hydrogen to hydrocarbon mole ratio may be from 0 (no added hydrogen) to about 10, with a preferred range of from 0 to about 3. A particularly preferred range of hydrogen to hydrocarbon mole ratio will be from 0 to about 2.

The following specific examples will serve to illustrate the process of the present invention, without unduly limiting same. In the examples, when Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078 and in *The Journal of Catalysis*, Vol. IV, pp. 522–529 (August 1965), each incorporated herein as to that description. It is noted that instrinsic rate constants for many acid-catalyzed reactions are proportional to the Alpha Value for a particular crystalline silicate catalyst (see "The Active Site of Acidic Aluminosilicate Catalysts," *Nature*, Vol. 309, No. 5959, pp. 589–591, 14 June 1984).

EXAMPLE 1

Five separate molecular sieves were prepared for testing of the present concept and comparisons to determine important process/catalyst limitations.

Molecular Sieve A

A 6.4 parts quantity, by weight, of water was mixed with 11.7 parts 50% NaOH, 10.6 $Al_2(SO_4)_3.14H_2O$ and 71.4 parts amorphous silica (46.5% solids) prepared by the neutralization of sodium silicate with sulfuric acid. The reaction mixture had a composition, in mole ratios of:

| |
|---|
| $SiO_2/Al_2O_3 = 30$ |
| $H_2O/SiO_2 = 5.76$ |
| $OH^-/SiO_2 = 0.072$ |
| $OH^-/H_2O = 0.013$ |

The reaction mixture was then heated to 350° F. and stirred in an autoclave at that temperature for crystallization. After full crystallinity was achieved, the resulting crystals were separated from remaining liquid by filtration, washed with water and dried.

Molecular Sieve B

A 7.3 parts quantity, by weight, of water was mixed with 12.8 parts 50% NaOH, 10.1 parts $Al_2(SO_4)_3.14H_2O$, 1.6 parts ZSM-5 seeds and 68.2 parts amorphous silica (47.6% solids) prepared by the neutralization of sodium silicate with sulfuric acid. The reaction mixture had a composition, in mole ratios, of:

| |
|---|
| $SiO_2/Al_2O_3 = 32$ |
| $H_2O/SiO_2 = 5.45$ |
| $OH^-/SiO_2 = 0.105$ |
| $OH^-/H_2O = 0.0192$ |

The reaction mixture was then heated directly to 220° F. and stirred in an autoclave at that temperature for crystallization. After full crystallinity was achieved, the resulting crystals were separated from remaining liquid by filtration, washed with water and dried.

Molecular Sieve C

A 3.1 parts quantity, be weight, of n-propylamine was added to a mixture containing 1.1 parts sodium chloride, 0.2 parts ZSM-5 seeds, 0.2 parts dispersant (mixture of polymerized aryl and substituted benzoid alkyl sulfonic acids), 2.6 parts $Al_2(SO_4)_3.14H_2O$, 7.0 parts 50% NaOH, 25.8 parts HiSil 233 (a precipitated hydrated $SiO_2$ containing about 6 wt. % free $H_2O$ and about 4.5 wt. % bound $H_2O$ of hydration and having an ultimate particle size of about 0.02 micron) and 59.9 parts water. The reaction mixture had a composition, in mole ratios, of:

$$SiO_2/Al_2O_3 = 65$$
$$H_2O/SiO_2 = 9.92$$
$$OH^-/SiO_2 = 0.163$$
$$N/Al_2O_3 = 9.2$$
$$OH^-/H_2O = 0.0165$$

wherein N is the n-propylamine. In the above ratios, the hydroxide concentration is based on only inorganic sources.

The reaction mixture was then heated direction to 220° F. and stirred in an autoclave at that temperature for crystallization. After full crystallinity was achieved, the resulting crystals were separated from remaining liquid by filtration, washed with water, exchanged with NH$_4$NO$_3$ and dried.

Molecular Sieve D

A 3.1 parts quantity, by weight, of n-propylamine was added to a mixture containing 1.1 parts sodium chloride, 0.2 parts ZSM-5 seeds, 0.2 parts dispersant (mixture of polymerized aryl and substituted benzoid alkyl sulfonic acids), 2.6 parts Al$_2$(SO$_4$)$_3$.14 H$_2$O, 7.0 parts 50% NaOH, 25.8 parts HiSil 233 and 59.9 parts water. The reaction mixture had a composition, in mole ratios, of:

$$SiO_2/Al_2O_3 = 65$$
$$H_2O/SiO_2 = 9.92$$
$$OH^-/SiO_2 = 0.163$$
$$N/Al_2O_3 = 9.2$$
$$OH^-/H_2O = 0.0165$$

wherein N is the n-propylamine. In the above ratios, the hydroxide concentration is based on only inorganic sources.

The reaction mixture was then heated directly to 320° F. and stirred in an autoclave at that temperature for crystallization. After full crystallinity was achieved, the resulting crystals were separated from remaining liquid by filtration, washed with water, exchanged with NH$_4$NO$_3$ and dried.

Molecular Sieve E

A 1.0 parts quantity, by weight, of water was mixed with 7.0 parts 100% NaOH, 10.8 parts Al$_2$(SO$_4$)$_3$.14 H$_2$O, 75.6 parts amorphous silica (45.2% solids) prepared by the neutralization of sodium silicate with sulfuric acid, and 5.5 parts ZSM-5 seeds (33% solids). The reaction mixture had a composition, in mole ratios, of:

$$SiO_2/Al_2O_3 = 31$$
$$H_2O/SiO_2 = 4.95$$
$$OH^-/SiO_2 = 0.109$$
$$OH^-/H_2O = 0.0219$$

The reaction mixture was then heated to 220° F. and stirred in an autoclave at that temperature for crystallization. After full crystallinity was achieved, the resulting crystals were separated from remaining liquid by filtration, washed with water and dried.

The above molecular sieve materials were evaluated for diffusion rate constants, composition, e.g. alumina, silica and sodium contents, surface area, particle density, pore volume and Alpha Value. Results of these evaluations are listed in Table II below.

TABLE II

| Molecular Sieve | A | B | C | D | E |
|---|---|---|---|---|---|
| SiO$_2$/Al$_2$O$_3$, mole ratio | 26 | 26 | 55 | 55 | 26 |
| Na, ppm | 135 | 120 | 450 | 280 | — |
| Diffusion rate constant (D/r$^2$ × 10$^6$), sec$^{-1}$ | <150 | >150 | >150 | <150 | >150 |
| Surface area, m$^2$/g | 325 | 317 | 349 | 265 | — |
| Particle density, g/cc | 0.87 | 1.01 | 0.88 | 0.93 | — |
| Pore volume, cc/g | 0.77 | 0.61 | 0.76 | 0.70 | — |
| Alpha Value | 650 | 710 | 350 | 290 | 427 |

EXAMPLE 2

The molecular sieves of Example 1 were each composited with binder alumina and made into extrudates such that Catalyst A comprised 65 wt. % Molecular Sieve A and 35 wt. % alumina, Catalyst B comprised 65 wt. % Molecular Sieve B and 35 wt. % alumina, Catalyst C comprised 65 wt. % Molecular Sieve C and 35 wt. % alumina, Catalyst D comprised 65 wt. % Molecular Sieve D and 35 wt. % alumina.

Each catalyst was then evaluated for toluene disproportionation in identical reactors and at identical reaction conditions. Each catalyst was diluted in the same fashion, 2.3 g Catalyst A with 4.5 g inert sand, 1.1 g Catalysts B,C and D with 1.0 cc inert vycor chips. The reactors were ⅜-inch o.d. stainless steel and the reaction conditions were 600 psig, 4.0 hr$^{-1}$ weight hourly space velocity (based on molecular sieve) and a hydrogen/hydrocarbon mole ratio of 2. Feedstock was dried toluene and a target toluene conversion of 48±1 wt. % was maintained. The toluene was dried for each reaction by percolating through activated alumina.

Liquid and gas products from the reactions were analyzed by conventional chromatography. Run data are presented in FIG. 1.

FIG. 1 is a plot of reaction temperature in °F. versus time on stream in days for each of the Example 2 disproportionation runs.

It is noted that for Catalyst A the start-of-cycle temperature was 750° F., which was maintained throughout the run. For Catalyst B, the initial start-of-cycle temperature was 730° F. Since Catalyst B aged rapidly, the temperature was corrected for the target conversion when necessary by using a factor of 3 wt. % toluene conversion/10° F. The same aging correction factor was used for the runs with Catalysts C and D. For Catalyst C, the start-of-cycle temprature was 849° F.; and for Catalyst D, 847° F. Catalyst E reached the 48% target conversion at 775° F. initially and aged to 802° F.

From the data plotted in FIG. 1, it is observed that Catalyst A showed no appreciable aging (<0.1° F./day) over a 30 day cycle. Catalyst E, with a silica/alumina mole ratio of 26, but a diffusion rate constant of greater than 150 sec$^{-1}$, aged 0.9° F./day over the 30 day cycle. Catalyst C, with a silica/alumina mole ratio of 55 and a diffusion rate constant of greater than 150 sec$^{-1}$, aged over 50° F. in the same 30 day time period, giving an aging rate of >1° F./day. Catalyst B, with a diffusion rate constant greater than 150 sec$^{-1}$, and Catalyst D, with a silica/alumina mole ratio of 55, both showed severe aging at a rate of >10° F./day.

It will be appreciated that the operating conditions for the reaction in accordance with the process of this invention, as exemplified in the foregoing examples, may be varied within the limits specified so that the process may be conducted in vapor-phase, and that various modifications and alterations may be made in the process without departing from the spirit and scope thereof.

What is claimed is:

1. In a process for vapor-phase disproportionation of toluene which comprises contacting toluene with a catalyst composition comprising a crystalline molecular sieve characterized by a silica/alumina mole ratio of greater than 12 and a Constraint Index of from about 1 to about 12 under conditions effective for accomplishing said vapor-phase disproportionation, the improvement wherein said molecular sieve as synthesized has a silica/alumina mole ratio of less than 55 and a diffusion rate constant of less than about 150 $sec^{-1}$.

2. The process of claim 1 wherein said molecular sieve has a silica/alumina mole ratio of from about 20 to about 40.

3. The process of claim 1 wherein said molecular sieve has a diffusion rate constant of less than about 120 $sec^{-1}$.

4. The process of claim 1 wherein said molecular sieve has the structure of ZSM-5, ZSM-11, ZSM-12, ZSM-5/ZSM-11 intermediate, ZSM-22, ZSM-23, ZSM-35, ZSM-38, ZSM-48, ZSM-50 or Beta.

5. The process of claim 1 wherein said molecular sieve has a silica/alumina mole ratio of from about 20 to about 40, a diffusion rate constant of less than about 120 $sec^{-1}$ and the structure of ZSM-5.

6. The process of claim 1 wherein said molecular sieve contains cations selected from the group consisting of hydrogen, hydrogen precursor, non-noble metal of Group VIII of the Periodic Table and the combinations thereof.

7. The process of claim 4 wherein said molecular sieve contains cations selected from the group consisting of hydrogen, hydrogen precursor, non-noble metal of Group VIII of the Periodic table and combinations thereof.

8. The process of claim 5 wherein said molecular sieve contains cations selected from the group consisting of hydrogen, hydrogen precursor, non-noble metal of Group VIII of the Periodic Table and combinations thereof.

9. The process of claim 1 wherein said conditions effective for accomplishing said vapor-phase disproportionation include a temperature of from about 600° F. to about 1100° F., a pressure of from about atmospheric to about 1000 psig, a hydrogen/hydrocarbon mole ratio of from 0 to about 10 and a weight hourly space velocity, based upon weight of active catalyst component, of from about 0.1 $hr^{-1}$ to about 30 $hr^{-1}$.

10. The process of claim 1 wherein said catalyst composition comprises said molecular sieve and a binder.

11. The process of claim 10 wherein said binder is selected from the group consisting of alumina, zirconia, silica, magnesia, thoria, titania, boria and a combination thereof.

12. The process of claim 11 wherein said binder comprises alumina.

13. The process of claim 1 wherein said catalyst composition is in the form of extrudate, beads or fluidizable microspheres.

14. In a process for vapor-phase disproportionation of toluene which comprises contacting toluene with a catalyst composition comprising a crystalline molecular sieve having the structure of ZSM-5, a silica/alumina mole ratio of greater than 12 and a Constraint Index of from about 1 to about 12 under conditions effective for accomplishing said vapor-phase disproportionation including a temperature of from about 600° F. to about 1100° F., a pressure of from about atmospheric to about 1000 psig, a hydrogen/hydrocarbon mole ratio of from 0 to about 10 and a weight hourly spaced velocity, based upon weight of active catalyst component, of from about 0.1 $hr^{-1}$ to about $30^{-1}$, the improvement wherein said crystalline molecular sieve as synthesized has a silica/alumina mole ratio of less than 55 and a diffusion rate constant of less than about 150 $sec^{-1}$.

15. In a process for vapor-phase disproportion of toluene which comprises contacting toluene with a catalyst composition comprising a crystalline molecular sieve having the structure of ZSM-5, a silica/alumina mole ratio of greater than 12 and a Constraint Index of from about 1 to about 12 under conditions effective for accomplishing said vapor-phase disproportionation including a temperature of from about 600° F. to about 1100° F., a pressure of from about atmospheric to about 1000 psig, a hydrogen/hydrocarbon mole ratio of from about 0 to about 10 and a weight hourly space velocity, based upon weight of active catalyst component, of from about $0.1^{-1}$ to about 30$hr^{-1}$ the improvement wherein said crystalline molecular sieve as synthesized has a silica/alumina mole ratio of from about 20 to about 40 and a diffusion rate constant of less than about 120 $sec^{-1}$.

* * * * *